(12) United States Patent
Stoval, III et al.

(10) Patent No.: US 11,152,121 B2
(45) Date of Patent: Oct. 19, 2021

(54) GENERATING CLINICAL SUMMARIES USING MACHINE LEARNING

(71) Applicant: International Business Machines Corporation, Armonk, NY (US)

(72) Inventors: William M. Stoval, III, Acton, MA (US); Marwan Sati, Mississauga (CA)

(73) Assignee: International Business Machines Corporation, Armonk, NY (US)

(*) Notice: Subject to any disclaimer, the term of this patent is extended or adjusted under 35 U.S.C. 154(b) by 310 days.

(21) Appl. No.: 16/263,411

(22) Filed: Jan. 31, 2019

(65) Prior Publication Data

US 2020/0251218 A1  Aug. 6, 2020

(51) Int. Cl.
*G16H 50/30* (2018.01)
*G06N 20/00* (2019.01)
*G16H 10/60* (2018.01)

(52) U.S. Cl.
CPC ............ *G16H 50/30* (2018.01); *G06N 20/00* (2019.01); *G16H 10/60* (2018.01)

(58) Field of Classification Search
CPC ........ G16H 50/30; G16H 10/60; G16H 50/20; G16H 15/00; G06N 20/00
See application file for complete search history.

(56) References Cited

U.S. PATENT DOCUMENTS 7,983,935 B1    7/2011  Carricarte et al.
8,612,261 B1 * 12/2013  Swanson ................ G16H 10/60
                                                 705/3
2002/0138524 A1  9/2002  Ingle et al.
2006/0080140 A1  4/2006  Buttner et al.
2008/0103828 A1  5/2008  Squilla et al.
2009/0178004 A1  7/2009  Stoval et al.

(Continued)

FOREIGN PATENT DOCUMENTS

KR    20090032337    4/2009
WO    WO-2018220550 A1 * 12/2018 ............ G16H 50/50

OTHER PUBLICATIONS

Patrick, Jon; Min Li. "An Ontology for clinical questions about the contents of patient notes." Journal of Biomedical Informatics 45. (2012) 292-306. (Year: 2012).*

(Continued)

*Primary Examiner* — Linh Giang Le
(74) *Attorney, Agent, or Firm* — Will Stock; Edell, Shapiro & Finnan, LLC

(57) ABSTRACT

A computer system generates a clinical summary for a patient based on machine learning. One or more templates are generated, each indicating medical information for a corresponding clinical summary with respect to a medical condition of a patient. Preferences for medical information for each corresponding clinical summary are learned based on a history of desired medical information for clinical summaries for the medical condition. The learned preferences are applied to the one or more templates. A clinical summary is generated with respect to the medical condition of the patient based on the one or more templates with the learned preferences. Embodiments of the present invention further include a method and program product for generating a clinical summary for a patient based on machine learning in substantially the same manner described above.

12 Claims, 5 Drawing Sheets

(56) References Cited

U.S. PATENT DOCUMENTS

2014/0108043 A1* 4/2014 Ach ...................... G06Q 10/10
                                                            705/3
2015/0370979 A1   12/2015 Boloor et al.
2016/0203281 A1    7/2016 Zalis et al.
2017/0061100 A1    3/2017 Sati
2018/0137943 A1    5/2018 Webb et al.

OTHER PUBLICATIONS

V. Lopez, "Note Highlights: Surfacing Relevant Concepts from Unstructured Notes for Health Professionals," 2017 IEEE International Conference on Healthcare Informatics (ICHI), Park City, UT, 2017, pp. 198-207.
R. Pivovarov, "Automated Methods for the Summarization of Electronic Health Records." Journal of the American Medical Informatics Association: JAMIA 22.5 (2015): 938-947.
T. Van Vleck, "Assessing Data Relevance for Automated Generation of A Clinical Summary." AMIA Annual Symposium Proceedings 2007 (2007): 761-765.

* cited by examiner

GENERATING CLINICAL SUMMARIES USING MACHINE LEARNING

BACKGROUND

1. Technical Field

Present invention embodiments relate to generating clinical summaries, and more specifically, to generating personalized clinical summaries using machine learning.

2. Discussion of the Related Art

A clinical summary is a synopsis of a patient's clinical history that includes health records. A clinical summary for a patient may include information such as the patient's identity, date of birth, reason for medical examination, vital signs, anatomical measurements, prior diagnoses, and the like. A clinician may often desire a concise clinical summary that contains only the information that the clinician deems relevant for the care of a particular patient. However, manually assembling a personalized clinical summary can be labor-intensive and costly, as the clinical summary may be personalized according to the preferences of the clinician, the patient history, the particular diagnostic or procedure being performed on the patient, and the like. Manual assembly of personalized clinical summary would require experts to create a template for each medical scenario as well as for each clinician, which is an impractical task even for small health care organizations.

SUMMARY

According to one embodiment of the present invention, a computer system generates a clinical summary for a patient based on machine learning. One or more templates are generated, each indicating medical information for a corresponding clinical summary with respect to a medical condition of a patient. Preferences for medical information for each corresponding clinical summary are learned based on a history of desired medical information for clinical summaries for the medical condition. The learned preferences are applied to the one or more templates. A clinical summary is generated with respect to the medical condition of the patient based on the one or more templates with the learned preferences. By using machine learning to generate personalized clinical summaries, the need for experts to create templates for personalized clinical summaries is eliminated. Furthermore, when clinical summaries are personalized to the preferences of clinicians, patients can be treated more quickly and more efficiently.

Various other embodiments of the present invention will now be discussed. In some embodiments, a personalized template is generated based on user indications of relevant medical information for the personalized template. By basing personalization of templates on user indications of relevance, irrelevant data may be omitted from clinical summaries, resulting in time savings for a health care organization. In some embodiments, a template is generated based on crowdsourced indications for medical information. Generating templates based on crowdsourced indications enables new users to be provided with clinical summaries that are still relevant to the user's area of practice before the user's preferences are learned. In some embodiments, templates are associated with a medical specialty and a corresponding medical scenario. By generating templates that are specialized for specific situations, clinicians are provided with relevant data, enabling clinicians to more quickly diagnose and treat patients. In some embodiments, machine learning is applied to analyze a medical scenario and to determine a corresponding template for producing the clinical summary with respect to the medical condition of a patient. By employing a machine learning model to analyze medical scenarios, templates can be customized to include specific details that are relevant for each medical scenario, thus providing personalized clinical summaries for any situation in a manner that is time-saving and inexpensive. In some embodiments, a machine learning model analyzes a medical scenario based on user feedback for the medical information and a set of parameters that include a reason for a medical examination, a complaint for the patient, a modality, a medical procedure, anatomy, automatic image findings based on image processing, information within a DICOM medical image header, information within a HL7 message, and anatomical measurements. By analyzing these parameters, the generation of personalized templates can be automated. Embodiments of the present invention further include a method and program product for generating a clinical summary for a patient based on machine learning in substantially the same manner described above.

BRIEF DESCRIPTION OF THE DRAWINGS

Generally, like reference numerals in the various figures are utilized to designate like components.

DETAILED DESCRIPTION

Figure 1:
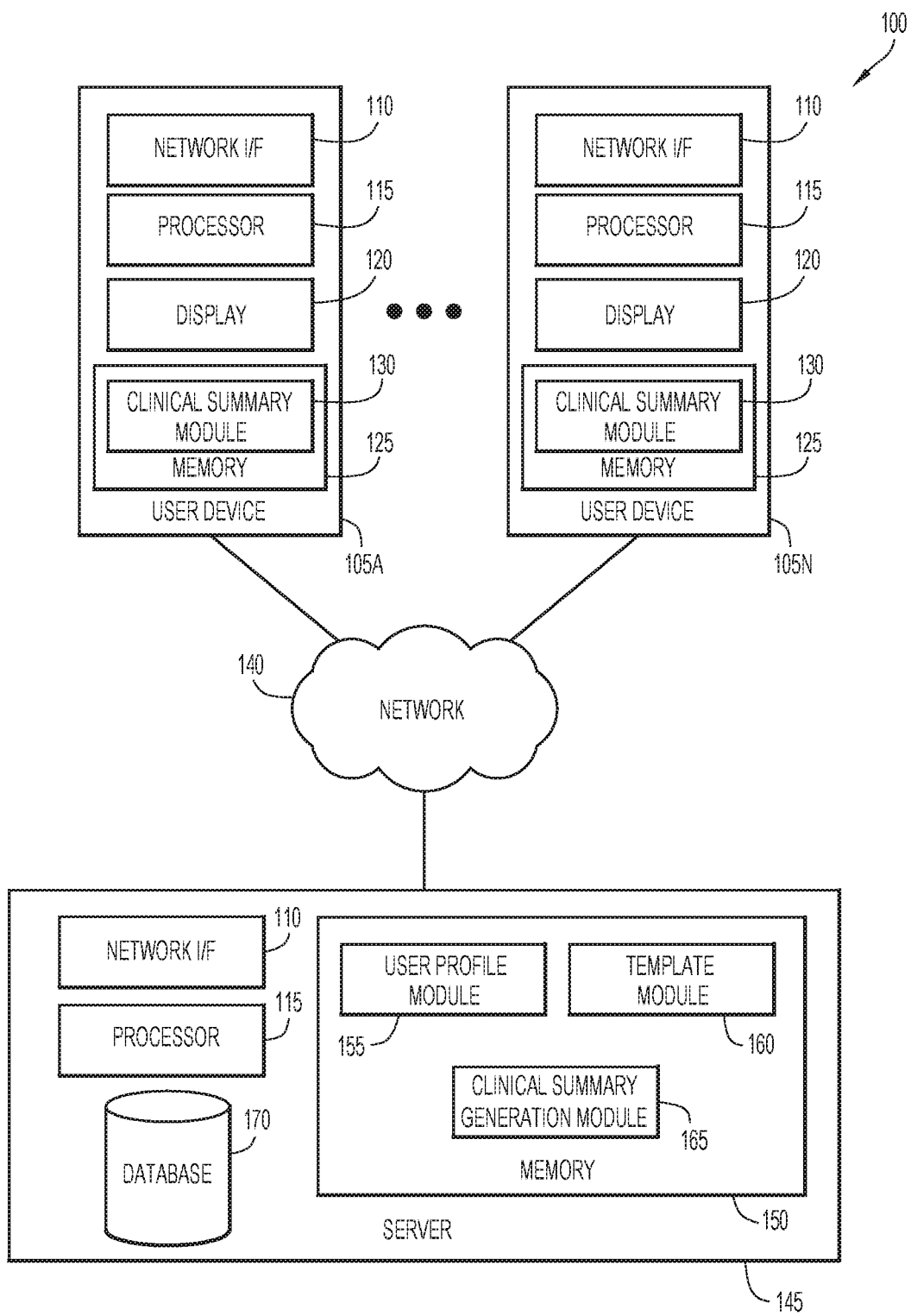
FIG. 1 is a block diagram depicting a computing environment for generating personalized clinical summaries in accordance with an embodiment of the present invention.

Present invention embodiments relate to generating clinical summaries, and more specifically, to generating personalized clinical summaries using machine learning. A generic clinical summary may contain superfluous information, forcing a clinician to search through an excessive amount of health records to find relevant information. In contrast, a personalized clinical summary may contain information that is relevant to a particular clinical context by omitting or de-emphasizing any irrelevant or extraneous information. A clinical summary may be personalized based on a role and sub-specialty of the clinician, a nature of an examination, a patient history, and the like. For example, a neuroradiologist may be interested in a patient's history of aneurysms and usage of blood-thinning medication, but may not be interested in the patient's allergies. Thus, a personalized clinical summary may satisfy the requirements of a clinician for a particular clinical setting, enabling a clinician to more quickly diagnose and treat a patient's condition.

However, each clinical context may differ from the next, making it extremely labor-intensive to manually construct a template of a clinical summary for each specific clinical context. Present invention embodiments utilize a machine learning model to generate personalized clinical summaries.

Default templates for clinical summaries are generated and refined using crowdsourced feedback, and templates are then personalized for a clinician that are specific to a particular clinical context and are based on learned preferences of the clinician. The template may then be populated with a patient's electronic health records to generate a personalized clinical summary. By generating personalized clinical summaries using machine learning, a clinician may more efficiently diagnose and treat patients, thereby enabling faster, less-costly provision of health care.

In some embodiments, a personalized template is generated based on user indications of relevant medical information for the personalized template. By basing personalization of templates on user indications of relevance, irrelevant data may be omitted from clinical summaries, resulting in time savings for a health care organization. In some embodiments, a template is generated based on crowdsourced indications for medical information. Generating templates based on crowdsourced indications enables new users to be provided with clinical summaries that are still relevant to the user's area of practice before the user's preferences are learned. In some embodiments, templates are associated with a medical specialty and a corresponding medical scenario. By generating templates that are specialized for specific situations, clinicians are provided with relevant data, enabling clinicians to more quickly diagnose and treat patients. In some embodiments, machine learning is applied to analyze a medical scenario and to determine a corresponding template for producing the clinical summary with respect to the medical condition of a patient. By employing a machine learning model to analyze medical scenarios, templates can be customized to include specific details that are relevant for each medical scenario, thus providing personalized clinical summaries for any situation in a manner that is time-saving and inexpensive. In some embodiments, a machine learning model analyzes a medical scenario based on user feedback for the medical information and a set of parameters that include a reason for a medical examination, a complaint for the patient, a modality, a medical procedure, anatomy, automatic image findings based on image processing, information within a DICOM medical image header, information within a HL7 message, and anatomical measurements. By analyzing these parameters, the generation of personalized templates can be automated.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Present invention embodiments will now be described in detail with reference to the Figures. FIG. 1 is a block diagram depicting a computing environment 100 for generating personalized clinical summaries in accordance with an embodiment of the present invention. As depicted, computing environment 100 includes user devices 105A-105N and a server 145. It is to be understood that the functional division among components of computing environment 100 have been chosen for purposes of explaining present invention embodiments and is not to be construed as a limiting example.

Each user device 105A-105N includes a network interface 110, at least one processor 115, a display 120, and memory 125. Memory 125 may include clinical summary module 130. Each user device 105A-105N may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 110 enables components of each user device 105A-105N to send and receive data over a network, such as network 140. Each user device 105 may include internal and external hardware components, as depicted and described in further detail with respect to FIG. 5.

Display 120 may include any electronic device capable of presenting information in a visual form. For example, display 120 may be a liquid crystal display (LCD), a cathode ray tube (CRT) display, a light-emitting diode (LED) display, an electronic ink display, and the like. Information relating to personalized clinical summaries may be presented to a user of each user device 105A-105N via display 120.

Clinical summary module 130 may include one or more modules or units to perform various functions of present invention embodiments described below. Clinical summary module 130 may be implemented by any combination of any quantity of software and/or hardware modules or units, and may reside within memory 125 of each user device 105A-105N for execution by a processor, such as processor 115.

Clinical summary module 130 may present clinical summaries to a user of any user device 105A-105N. A clinical summary may include electronic health care records relating to a patient. Clinical summary module 130 may process queries provided by a user to retrieve information relating to clinical summaries. A user of any user device 105A-105N may input a query that comprises a patient name or other identifier for a patient in order to retrieve health care information relating to that patient. Clinical summary module 130 may receive information relating to clinical summaries from an electronic health care record database, such as database 170. When a user utilizes any user device 105A-105N, clinical summary module 130 may present a clinical summary that is personalized for the user. Clinical summary module 130 may present clinical summaries via a graphical user interface that includes one or more elements by which a user may provide feedback. A user may indicate that a selected field contains health information that is either relevant or irrelevant to the user's clinical practice. A user interface for presenting clinical summaries and receiving feedback information is depicted and described in further detail with respect to FIG. 4.

Network 140 may include a local area network (LAN), a wide area network (WAN) such as the Internet, or a combination of the two, and includes wired, wireless, or fiber optic connections. In general, network 140 can be any combination of connections and protocols known in the art that will support communications between user devices 105A-105N and/or server 145 via their respective network interfaces 110 in accordance with embodiments of the present invention.

Server 145 includes a network interface 110, at least one processor 115, memory 150, and a database 170. Memory 150 includes a user profile module 155, template module 160, and clinical summary generation module 165. In various embodiments of the present invention, server 145 may include a laptop computer, a tablet computer, a netbook computer, a personal computer (PC), a desktop computer, a personal digital assistant (PDA), a smart phone, or any programmable electronic device capable of executing computer readable program instructions. Network interface 110 enables components of server 145 to send and receive data over a network, such as network 140. Server 145 may include internal and external hardware components, as depicted and described in further detail with respect to FIG. 5.

User profile module 155, template module 160, and clinical summary generation module 165 may include one or more modules or units to perform various functions of present invention embodiments described below. User profile module 155, template module 160, and clinical summary generation module 165 may be implemented by any combination of any quantity of software and/or hardware modules or units, and may reside within memory 150 of server 145 for execution by a processor, such as processor 115.

User profile module 155 may create and manage user profiles for clinicians. When a clinician registers a user account via any user device 105A-105N, user profile module 155 may collect information relating to the clinician, such as the clinician's role, areas of specialty, and preferences. As a clinician provides feedback regarding the clinician's preferences for clinical summaries, user profile module 155 stores the preferences on the clinician's user profile. User profile module 155 may associate personalized templates with a user profile in order to present personalized clinical summaries to a user. For example, when a user utilizes a user device, such as user device 105A, the user's personalized templates will be populated with electronic health records of queried patients to provide the user with personalized clinical summaries.

Template module 160 may generate and modify templates for the creation of personalized clinical summaries. Template module 160 may generate default templates for a particular role and sub-specialty of a user, and may modify default templates based on a user's preferences. A template may be a listing of fields that can be populated with electronic health record information to produce a clinical summary. Each template may contain a patient name field and one or more fields that contain health records of the patient. Template module 160 may generate default templates for one or more roles and sub-specialties by using a machine learning model to analyze crowdsourced feedback data. A new user may first be provided with default templates, and based on the user's feedback, template module 160 will utilize machine learning to create personalized templates for the user.

Default templates may be initially generated by using a machine learning model to analyze crowdsourced feedback information received by template module 160. A user of any user device 105A-105N may indicate whether a given field of a clinical summary is relevant or irrelevant to the user's area of practice and the clinical context. The indications of users may be fed into a machine learning model to determine which fields to include in a template for a specific area of practice and clinical context. For example, in a given clinical context (such as a type of spinal injury), there may be eighteen fields that 90% of neuroradiologists indicate as relevant, two fields that 50% of neuroradiologists indicate as relevant, and several more fields that fewer than 10% of neuroradiologists indicate as relevant. Template module 160 may process the feedback to generate a default template that includes the twenty fields that were indicated as relevant by a majority of the users.

Template module 160 may analyze a user's feedback to generate a personalized template for the user for any given clinical context. When a user is presented with a clinical summary based on a default template, the user may indicate which information the user considers to be relevant and irrelevant. A machine learning model may learn the user's preferences over time in order to generate personalized templates that include information deemed relevant by the user, and to omit or de-emphasize any information that the user has deemed irrelevant.

In order to determine a clinical context, template module 160 may use machine learning-based recognition to analyze a medical scenario. Template module 160 may process information including a reason for a medical examination, a complaint of a patient, modality information (e.g., methods of diagnoses), medical procedure information, anatomical information, automatic image findings extracted by processing medical images, information within a Digital Imaging and Communications in Medicine (DICOM) header, information in a Health Level Seven (HL7) message, and the like.

Clinical summary generation module 165 may generate clinical summaries using templates. Each template may be a default template or a template that is personalized for a particular user and clinical context by template module 160. Clinical summary generation module 165 may generate a clinical summary by populating the fields of a template with a patient's electronic health records. Clinical summary generation module 165 may fetch electronic health records from a database, such as database 170 and/or any other database accessible via network 140.

As an example, a template that is personalized for cardiology may have a patient identifier field, an age field, a heart rate field, a blood pressure field, an oxygen saturation field, a list of prescribed medications field, an anatomical measurements field, and the like. Clinical summary generation module 165 may generate a personalized clinical summary using the template by fetching electronic health records for a patient and populating the fields with the fetched data. Thus, clinical summary generation module 165 may produce a personalized clinical summary that includes a patient's name and/or hospital identification number, the patient's age, the patient's heart rate metrics, the patient's blood pressure metrics, the patient's oxygen saturation metrics, any medications prescribed to the patient, and the patient's anatomical measurements, such as height and weight.

Database 170 may include any non-volatile storage media known in the art. For example, database 170 can be implemented with a tape library, optical library, one or more independent hard disk drives, or multiple hard disk drives in a redundant array of independent disks (RAID). Similarly, data on database 170 may conform to any suitable storage architecture known in the art, such as a file, a relational database, an object-oriented database, and/or one or more tables. Database 170 may store data relating to the personalization of clinical summaries, including electronic health records, default and personalized templates for clinical summaries, crowdsourced feedback information, user preference information, and the like.

Figure 2:
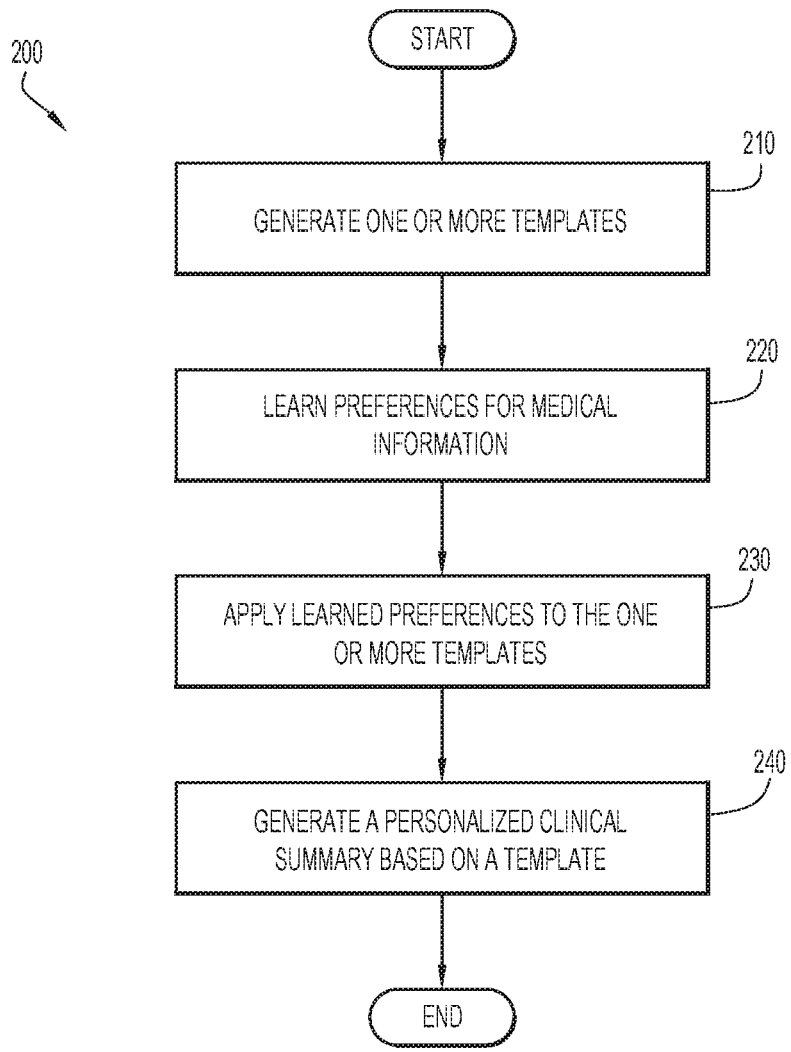
FIG. 2 is a flow chart depicting a method of generating a clinical summary in accordance with an embodiment of the present invention.

FIG. 2 is a flow chart depicting a method 200 of generating a clinical summary in accordance with an embodiment of the present invention.

One or more templates are generated at operation 210. One or more templates may be generated for each area of specialty based on crowdsourced feedback from users. Generated templates may be default templates that are generated for a level of specificity and/or for a medical scenario; for example, a default template may be generated for oncology in general, or templates may be generated for each sub-specialty of oncology, such as a default template for pediatric oncology, another default template for hematological oncology, and the like. In some embodiments, the generated template is a template that has already been personalized for a user to a degree. The generation of default templates is depicted and described in further detail with respect to FIG. 3.

A user's preferences for medical information are learned at operation 220. A user may initially be provided with a clinical summary generated using a default template that is selected based on the user's area of specialty and the particular medical scenario of a patient. As a user reviews the clinical summary, the user may provide feedback for each field of the clinical summary to indicate whether the user finds the information relevant or irrelevant. Template module 160 may then analyze a user's feedback using a machine learning model to learn the user's preferences regarding the relevance of information. In some embodiments, the machine learning model utilizes rules-based machine learning. For example, when a user indicates that the user finds information in a particular field to be relevant to a medical scenario of the patient, template module 160 may learn this preference. Likewise, when a user indicates that a field contains irrelevant information, template module 160 may learn that the user prefers to not be presented with the field.

The learned preferences of a user are applied to one or more templates at operation 230. Template module 160 may update one or more templates to reflect a user's learned preferences by adding or removing one or more fields to the template. Template module 160 may use machine learning to update templates for various medical scenarios by processing parameters such as a reason for an examination, a modality, a procedure, anatomical information, automatic image findings generated by image processing techniques, and the like. When a user indicates a preference for a particular medical scenario, template module 160 may adjust the template corresponding to that medical scenario as well as any templates for related medical scenarios. For example, template module 160 may apply any learned preferences for a template relating to a greenstick fracture of the tibia to a similar template relating to a greenstick fracture of the fibula.

In some embodiments, learned preferences are applied to one or more templates using a machine learning autoencoder model that includes an encoder layer and a decoder layer. The machine learning model may be used to predict a subset of the most relevant data elements for a current patient by scoring each data element. Each element may also receive a label indicating whether or not the element is predicted to be selected as a relevant element. Supervised training is employed to maximize the likelihood that the predictive labels are accurate. The data elements are input into the autoencoder model to decode the relevant data. In some embodiments, the machine learning model is trained using pairs of electronic medical record datasets with summary datasets that have been selected by a subject matter expert, and a network may be created for each category of chief complaint of a patient (e.g., reason for visit). In some embodiments, a single network may be created for all chief complaints, and each chief complaint may be assigned a weight to determine the likelihood that the predictive labels are accurate.

A personalized clinical summary based on a template is generated at operation 240. Clinical summary generation module 165 may generate clinical summary by populating a template that is personalized for a user and for a medical scenario. Each field of the template may be populated with corresponding electronic health records in order to generate the personalized clinical summary. Personalized clinical summaries may be presented to a user of any user device 105A-105N via display 120.

Figure 3:
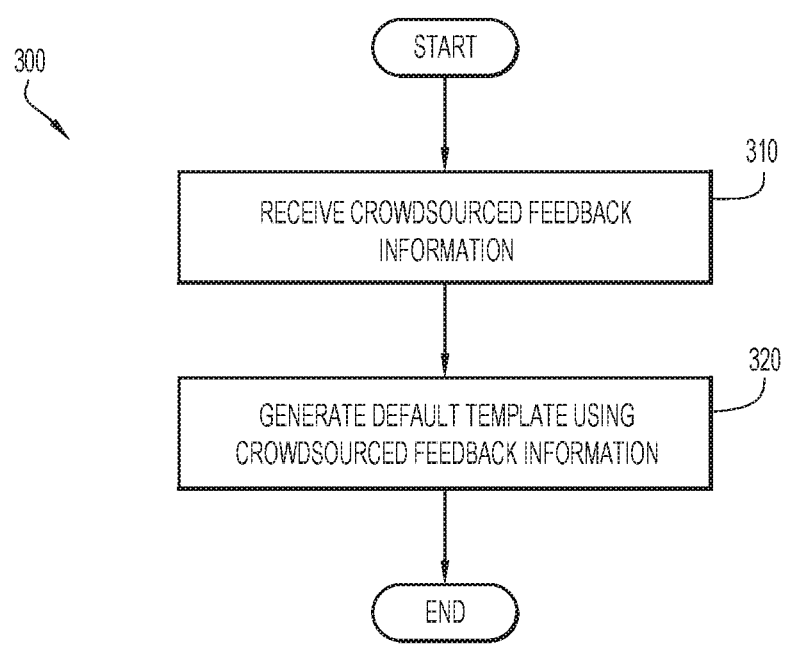
FIG. 3 is a flow chart depicting a method of generating a default template in accordance with an embodiment of the present invention.

FIG. 3 is a flow chart depicting a method 300 of generating a default template in accordance with an embodiment of the present invention.

Crowdsourced feedback information is received at operation 310. When a user reads a clinical summary on a user device, such as user device 105A, the user may provide feedback indicating whether the user found certain fields to be relevant or irrelevant. Crowdsourced feedback information may be organized according to the area of specialty of the clinician providing the feedback as well as the medical scenario. In some embodiments, server 145 may receive crowdsourced feedback information from multiple users via user devices 105A-105N.

A default template is generated using the crowdsourced feedback information at operation 320. A default template may be generated for each area of specialty and/or for each medical scenario. Template module 160 may process crowdsourced feedback information using known or other machine learning techniques in order to determine which fields will be present in a default template. Templates may include fields that a threshold amount of users have indicated to be relevant, and may omit fields that a threshold amount of users have indicated to not be relevant. For example, if 80% of clinicians of a particular specialty indicate that a particular field is relevant, that field may be included in default templates for that specialty.

Figure 4:
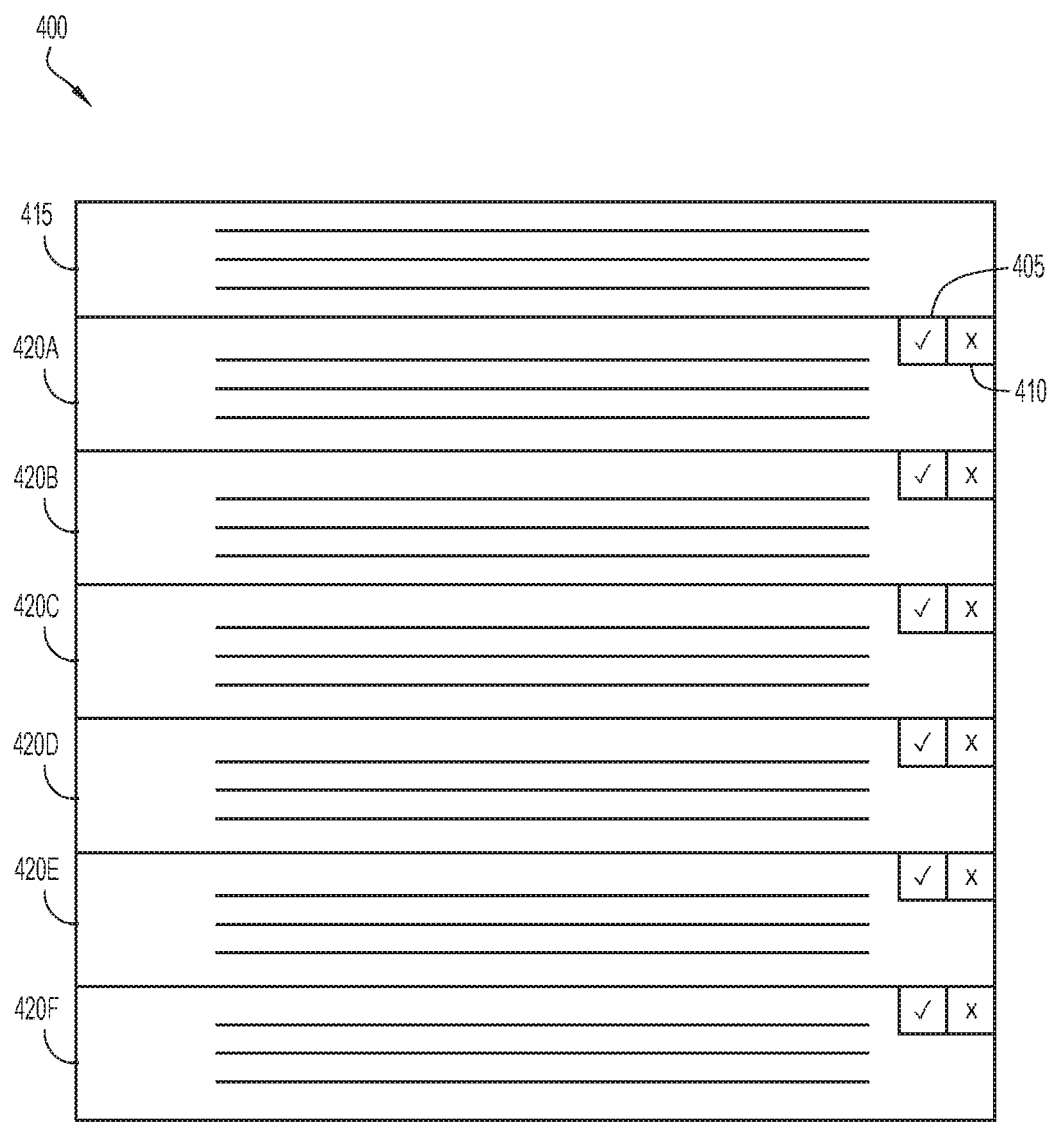
FIG. 4 is an example of a user interface in accordance with an embodiment of the present invention.

FIG. 4 is an example of a user interface 400 in accordance with an embodiment of the present invention. User interface 400 includes a display field element 405, a hide field element 410, an identification field 415, and one or more information fields 420A-420F. User interface 400 may present clinical summary information to a user, and may receive user feedback. User interface 400 may be presented to a user via display 120 of any user device 105A-105N. Identification information relating to a patient, such as the patient's name or other identifying information, may be presented in identification field 415.

A clinical summary may be presented on user interface 400. A user may interact with display field element 405 and hide field element 410 to indicate the relevance of each associated information field 420A-420F for the current medical scenario. Information fields 420A-420F may correspond to any field for one or more electronic health records. For example, information field 420A may include anatomical measurements, information field 420B may include blood testing information, information field 420C may include pulse, blood pressure, and temperature information, and the like. If a user wishes to always see an information field, such as information fields 420A and 420B, then the user may actuate the display field element 405 for those fields. Similarly, if a user does not want to view an information field, then the user may select the hide field element 410 corresponding to that field. In some embodiments, when a user selects a hide field element 410, the field may be omitted from the clinical summary that the user is currently viewing.

Figure 5:
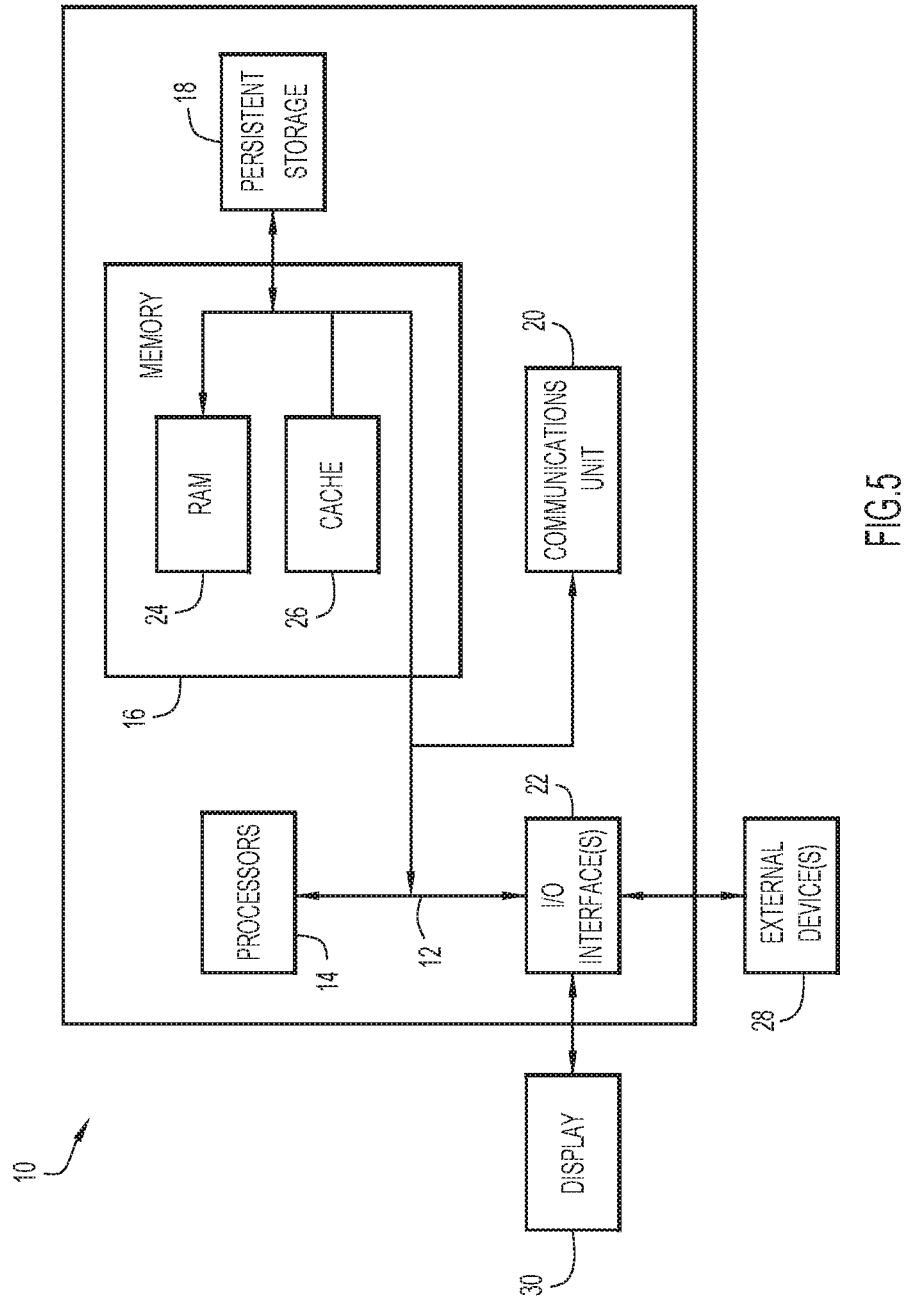
FIG. 5 is a block diagram depicting a computing device in accordance with an embodiment of the present invention.

FIG. 5 is a block diagram depicting components of a computer 10 suitable for executing the methods disclosed herein. Computer 10 may implement user devices 105A-105N and/or server 145 in accordance with embodiments of the present invention. It should be appreciated that FIG. 5 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to personalized clinical summaries (e.g., electronic health records, default and personalized templates for clinical summaries, crowdsourced feedback information, user preference information, etc.) may be stored within any conventional or other data structures (e.g., files, arrays, lists, stacks, queues, records, etc.) and may be stored in any desired storage unit (e.g., database, data or other repositories, queue, etc.). The data transmitted between user devices 105A-105N and/or server 145 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to personalized clinical summaries (e.g., electronic health records, default and personalized templates for clinical summaries, crowdsourced feedback information, user preference information, etc.) may include any information provided to, or generated by, user devices 105A-105N and/or server 145. Data relating to personalized clinical summaries may include any desired format and arrangement, and may include any quantity of any types of fields of any size to store any desired data. The data relating to personalized clinical summaries may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to personalized clinical summaries), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of generating personalized clinical summaries.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., server software, networking software, clinical summary module 130, user profile module 155, template module 160, clinical summary generation module 165, etc.). These systems may include any types of monitors and input devices (e.g., keyboard, mouse, voice recognition, etc.) to enter and/or view information.

It is to be understood that the software (e.g., server software, networking software, clinical summary module 130, user profile module 155, template module 160, clinical summary generation module 165, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., server software, networking software, clinical summary module 130, user profile module 155, template module 160, clinical summary generation module 165, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to personalized clinical summaries). The database system may be implemented by any number of any conventional or other databases, data stores or storage structures (e.g., files, databases, data structures, data or other repositories, etc.) to store information (e.g., data relating to personalized clinical summaries). The database system may be included within or coupled to the server and/or client systems. The database systems and/or storage structures may be remote from or local to the computer or other processing systems, and may store any desired data (e.g., data relating to personalized clinical summaries).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create mechanisms for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method of generating a clinical summary for a patient based on machine learning comprising:
    generating, via a processor, one or more templates each indicating medical information for a corresponding clinical summary with respect to a medical scenario of a patient, wherein the one or more templates are generated based on crowdsourced indications for the medical information, the crowdsourced indications received from a plurality of users associated with a plurality of medical specialties;
    learning, via the processor, preferences for medical information for each corresponding clinical summary based on a history of desired medical information for clinical summaries for the medical scenario;
    applying, via the processor, the learned preferences to the one or more templates; and
    generating, via the processor, a clinical summary with respect to the medical scenario of the patient based on the one or more templates with the learned preferences, wherein the clinical summary is generated by applying machine learning to analyze the medical scenario and to determine a corresponding template for producing the clinical summary with respect to the medical scenario of the patient, and wherein the medical scenario is analyzed based on user feedback from multiple users and a set of parameters for the medical scenario, the set of parameters including one or more of: a reason for a medical examination, a complaint for the patient, a modality, automatic image findings based on image processing, information within a DICOM medical image header, information within a HL7 message, and anatomical measurements.

2. The computer-implemented method of claim 1, wherein generating the one or more templates comprises:
generating a personalized template based on user indications of relevant medical information for the personalized template.

3. The computer-implemented method of claim 1, wherein the one or more templates are associated with a medical specialty and a corresponding medical scenario.

4. The computer-implemented method of claim 1, wherein the user feedback from multiple users includes an indication of a medical specialty for each user.

5. A computer system for generating a clinical summary for a patient based on machine learning, the computer system comprising:
one or more computer processors;
one or more computer readable storage media;
program instructions stored on the one or more computer readable storage media for execution by at least one of the one or more computer processors, the program instructions comprising instructions to:
generate one or more templates each indicating medical information for a corresponding clinical summary with respect to a medical scenario of a patient, wherein the one or more templates are generated based on crowdsourced indications for the medical information, the crowdsourced indications received from a plurality of users associated with a plurality of medical specialties;
learn preferences for medical information for each corresponding clinical summary based on a history of desired medical information for clinical summaries for the medical scenario;
apply the learned preferences to the one or more templates; and
generate a clinical summary with respect to the medical scenario of the patient based on the one or more templates with the learned preferences, wherein the clinical summary is generated by applying machine learning to analyze the medical scenario and to determine a corresponding template for producing the clinical summary with respect to the medical scenario of the patient, and wherein the medical scenario is analyzed based on user feedback from multiple users and a set of parameters for the medical scenario, the set of parameters including one or more of: a reason for a medical examination, a complaint for the patient, a modality, automatic image findings based on image processing, information within a DICOM medical image header, information within a HL7 message, and anatomical measurements.

6. The computer system of claim 5, wherein the instructions to generate the one or more templates comprise instructions to:
generate a personalized template based on user indications of relevant medical information for the personalized template.

7. The computer system of claim 5, wherein the one or more templates are associated with a medical specialty and a corresponding medical scenario.

8. The computer system of claim 5, wherein the user feedback from multiple users includes an indication of a medical specialty for each user.

9. A computer program product for generating a clinical summary for a patient based on machine learning, the computer program product comprising one or more computer readable storage media collectively having program instructions embodied therewith, the program instructions executable by a computer to cause the computer to:
generate one or more templates each indicating medical information for a corresponding clinical summary with respect to a medical scenario of a patient, wherein the one or more templates are generated based on crowdsourced indications for the medical information, the crowdsourced indications received from a plurality of users associated with a plurality of medical specialties;
learn preferences for medical information for each corresponding clinical summary based on a history of desired medical information for clinical summaries for the medical scenario;
apply the learned preferences to the one or more templates; and
generate a clinical summary with respect to the medical scenario of the patient based on the one or more templates with the learned preferences, wherein the clinical summary is generated by applying machine learning to analyze the medical scenario and to determine a corresponding template for producing the clinical summary with respect to the medical scenario of the patient, and wherein the medical scenario is analyzed based on user feedback from multiple users and a set of parameters for the medical scenario, the set of parameters including one or more of: a reason for a medical examination, a complaint for the patient, a modality, automatic image findings based on image processing, information within a DICOM medical image header, information within a HL7 message, and anatomical measurements.

10. The computer program product of claim 9, wherein the instructions to generate the one or more templates comprise instructions to:
generate a personalized template based on user indications of relevant medical information for the personalized template.

11. The computer program product of claim 9, wherein the one or more templates are associated with a medical specialty and a corresponding medical scenario.

12. The computer program product of claim 9, wherein the user feedback from multiple users includes an indication of a medical specialty for each user.

* * * * *